United States Patent [19]

Oono et al.

[11] Patent Number: 5,254,462
[45] Date of Patent: Oct. 19, 1993

[54] ANIMAL CELL LINE USEFUL FOR EXPRESSION OF EXOGENOUS GENES

[75] Inventors: Tadao Oono; Kaoru Saijo; Junko Kurashima, all of Ushiku, Japan

[73] Assignee: Rikagaku Kenkyusho, Wako, Japan

[21] Appl. No.: 714,639

[22] Filed: Jun. 13, 1991

[30] Foreign Application Priority Data

Oct. 23, 1990 [JP] Japan .................. 2-285171
May 14, 1991 [JP] Japan .................. 3-107932

[51] Int. Cl.$^5$ .................. C12P 21/02; C12N 5/10; C12N 15/63
[52] U.S. Cl. .................. 435/69.1; 435/240.2; 435/172.3
[58] Field of Search .................. 435/240.2, 172.3, 69.1

[56] References Cited

U.S. PATENT DOCUMENTS 4,741,901  5/1988  Levinson et al. .................. 424/88

FOREIGN PATENT DOCUMENTS

WO89/01028  2/1989  PCT Int'l Appl. .
WO89/01038  2/1989  PCT Int'l Appl. .
WO89/05862  6/1989  PCT Int'l Appl. .
2196348  4/1988  United Kingdom .

OTHER PUBLICATIONS

Tegtmeyer, *J. Virol.* vol. 15, 1975, pp. 613–618.
Pavlakis et al., from *Gene Transfer Vectors for Mammalian Cells*, 1987, Cold Spring Harbor Laboratory, pp. 29–38.
Cytotechnology, vol. 4, No. 3, Mar. 1990, pp. 279–283, R. Bliem, et al., "Antibody Production in Packed Bed Reactors Using Serum-Free and Protein-Free Medium".
Molecular & Cellular Biology, vol. 5, No. 3, Mar. 1985, pp. 563–568, H. Ariga, et al., "Cloned Mouse DNA Fragments Can Replicate in a Simian Virus 40 T Antigen-Dependent System in Vivo and in Vitro".
Gene, vol. 59, No. 2–3, 1987, pp. 231–239, U. H. Weidle, et al., "Establishment of a Temperature-Inducible Cell Line for Human Plasminogen Activator (Tissue-Type) by Transfection of Monkey Cells with Expression Constructs".
Gene, vol. 43, No. 3, 1986, pp. 237–245, F. G. Kern, et al., "An Inducible Eukaryotic Host-Vector Expression System: Amplification of Genes Under the Control of the Polyoma Late Promoter in a Cell Line Producing a Thermolabile Large . . . ".

*Primary Examiner*—Richard A. Schwartz
*Assistant Examiner*—James Ketter
*Attorney, Agent, or Firm*—Oblon, Spivak, McClelland, Maier & Neustadt

[57] ABSTRACT

The present invention relates to an animal cell line which is capable of growing in a substantially protein-free medium and has a substance capable of enhancing replication of exogenous genes.

The animal cell line according to the present invention can grow in a substantially protein-free medium and can replicate exogenous genes extrachromosomally. It is possible to easily produce a great amount of substances useful to mammals by using the transformant according to the present invention. Further, it is easy to collect and purify the substances useful to mammals, which are produced by using the transformant according to the present invention.

7 Claims, 4 Drawing Sheets

RESTRICTION MAP OF PLASMID pSVtsA58ori(−)−1

RESTRICTION MAP OF PLASMID pSVtsA58ori(−)−2

RESTRICTION MAP OF PLASMID pXGH5ori

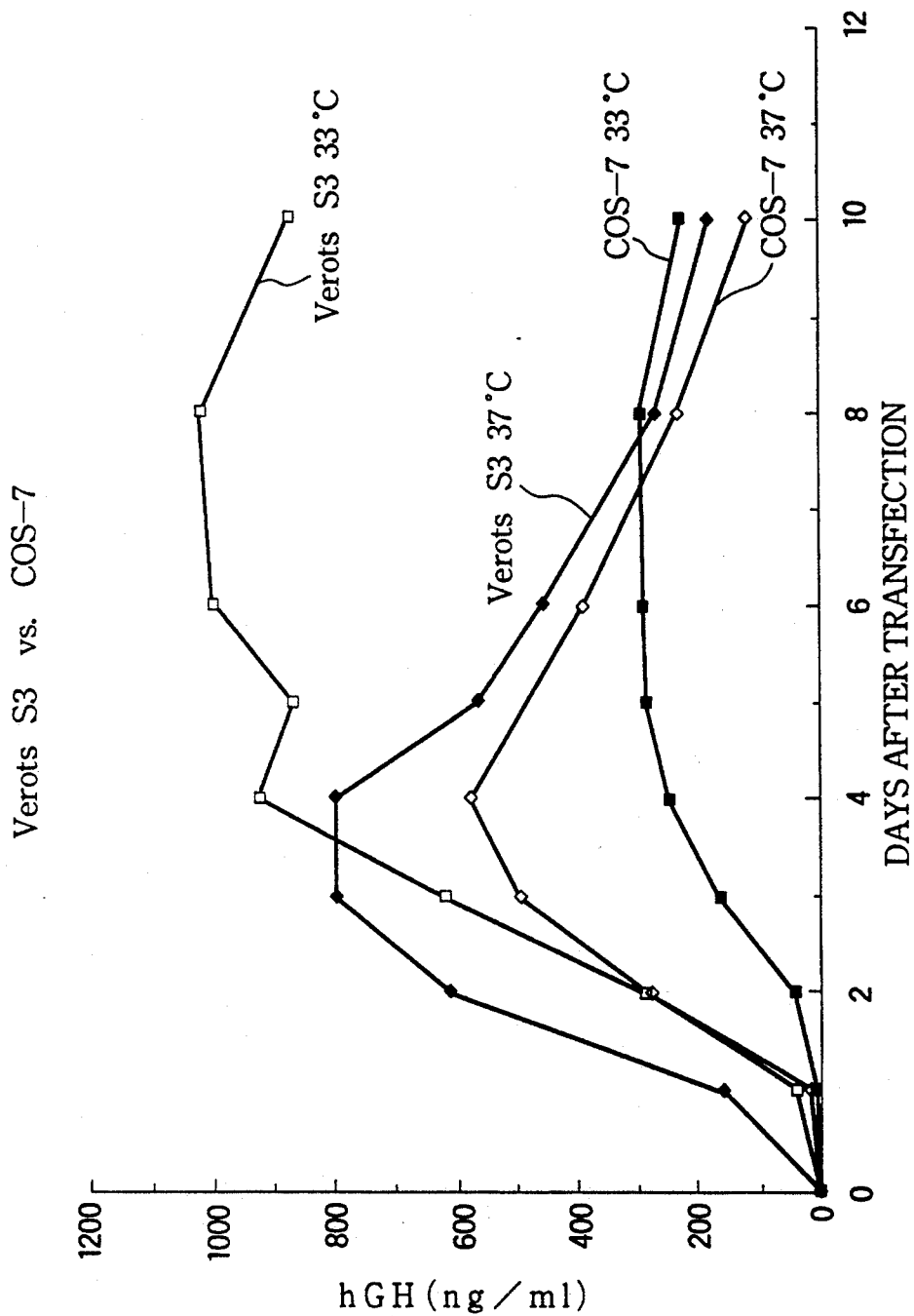

ANIMAL CELL LINE USEFUL FOR EXPRESSION OF EXOGENOUS GENES

BACKGROUND OF THE INVENTION

1. Field of the Invention

The present invention relates to an animal cell line which is capable of growing in a substantially protein-free medium and has a substance capable of enhancing replication of exogenous genes, a transformant obtained by transfecting said animal cell line with a recombinant DNA containing at least one exogenous gene capable of expression, a method of producing exogenous gene products by using the transformant, a method of using the animal cell line for preparing said transformant and a method of using said transformant for producing the exogenous gene products.

2. Description of the Prior Art

Recombinant DNA procedures have been widely used which comprise the steps of transfecting a DNA containing a specific gene(s) into a cultured cell, culturing the cell to express the gene products and obtaining the products.

Most of cultured animal cells useful for recombinant DNA procedures are cultured in a medium containing natural products of which the chemical composition is unknown, such as serum. For example, it is known that COS-1 cell line which was modified to produce mouse interferon γ is cultured in serum-containing Dulbecco's modified minimum essential medium (P. W. Gray, D.V. Goeddel., Proc. Natl, Acad. Sci. U.S.A., 80: 5842–5846, 1983). Thus, great efforts are required to remove impurities when collecting and purifying gene products. At the present time, there have been used processes wherein a cell transfected to express gene products is generally cultured first in a serum-containing medium and then in a serum-free medium to thereby easily collect and purify the gene products However, when a serum-containing medium is changed to a serum-free medium, the proliferation potency of the cultured cell decreases rapidly. In order to prevent this decrease, one needs to add proteins, such as insulin, transferrin, albumin and the like, to the serum-free medium. Addition of these proteins increases the cost of the medium because these proteins are more difficult to purify and more expensive than other low molecular components of the medium.

Vero-317 cell line derived from African green monkey kidney, L-P3 cell line derived from mouse and HeLa-P3 cell line derived from human cervix carcinoma and the like are known as animal cell lines which can grow in protein-free media. However, it has not been reported that these cells amplify exogenous genes extrachromosomally.

Some virus DNAs which can be used as vectors in recombinant DNA procedures are amplified in a host cell without being integrated in the nuclear chromosome of the host cell. For example, when a double-stranded circular DNA containing an origin of DNA replication of SV40 virus is transfected into a monkey cell having a large T antigen derived from SV40 virus, the DNA is replicated and amplified in the host monkey cell without being integrated in the nuclear chromosome of the host monkey cell (edited by Uchida, Oishi, Furusawa., "Use and Practice Mannual of Animal Cells"., PP 388–393, L.I.C.Co., 1984). Further, when a Baculo virus DNA is transfected into an insect cell, the DNA is replicated and amplified in the host insect cell without being integrated in the nuclear chromosome of the host insect cell (Maeda., Experimental Medicine., vol. 7, No. 13, 146–151, 1989; Sekine et al., Gene., vol. 65, 187, 1988; and Miyajima et al., Gene., Vol. 58, 273, 1987).

So far, an animal cell line has not been known which can grow in a substantially protein-free medium and can amplify transfected genes extrachromosomally.

SUMMARY OF THE INVENTION

Accordingly, an object of the present invention is to provide an animal cell line which can grow in a substantially protein-free medium and can amplify transfected genes extrachromosomally.

Another object of the present invention is to provide a transformant of the above animal cell line, which is obtained by transfecting the animal cell line with a recombinant DNA containing at least one exogenous gene capable of expression.

Yet object of the present invention is to provide a method of producing exogenous gene products by using the transformant.

A further object of the present invention is to provide a method of using the above animal cell line for preparing the transformant.

A still further object of the present invention is to provide a method of using said transformant for producing exogenous gene products.

Further objects, features and advantages of the present invention will become apparent from the Detailed Description of the preferred Embodiments which follow when considered together with the illustrative examples.

BRIEF DESCRIPTION OF THE DRAWINGS

FIG. 4 shows the concentration of human growth hormone in a culture supernatant of Verots-S3 cells or COS-7 cells against days after tranfection of pXGH5ori.

DETAILED DESCRIPTION OF THE PREFERRED EMBODIMENTS

Figure 1:
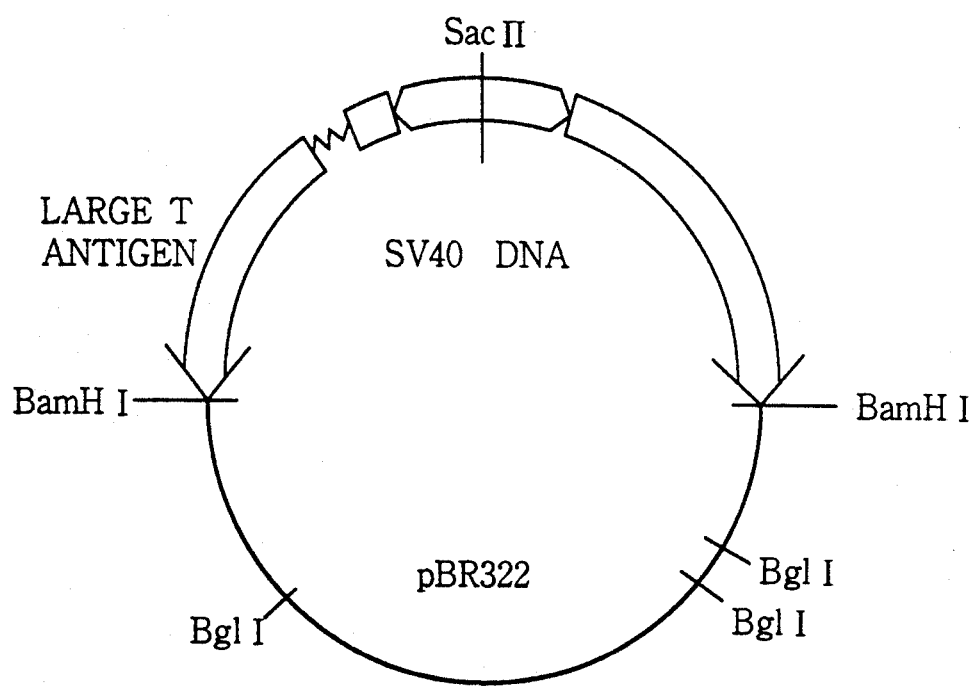
FIG. 1 shows a restriction map of plasmid pSvtsA5-8ori(−)−1.

The inventors have conducted various investigations and have found that an animal cell line which can grow in a substantially protein-free medium and has a substance capable of enhancing replication of exogenous genes can replicate the genes extrachromosomally. The goal of the present invention has therefore been accomplished.

A transformant which is obtained by transfecting a recombinant DNA containing at least one exogenous gene capable of expression into the animal cell line according to the present invention can grow in a substantially protein-free medium and express a great amount of exogenous gene products.

The present invention will be hereinafter explained in detail.

The animal cell line which is capable of growing in a substantially protein-free medium and has a substance capable of enhancing replication of exogenous genes can be prepared as follows.

First, an animal cell line which can grow in a substantially protein-free medium is provided. The "protein" includes a protein component such as insulin, transferrin, albumin, fibronectin, vitronectin, epidermal growth factor, insulin-like growth factor, fibroblast growth factor and the like as well as a natural product of which chemical composition is unknown, such as serum, plasma, milk and the like. The "substantially protein-free medium" means a medium which contains proteins in an amount of from 0 to 0.001% (W/V), preferably 0% (W/V). Examples of the protein-free media include a minimum essential medium to which biotin is added in a final concentration of 0.02 mg/l (hereinunder referred to as "bMEM"), DM-160 medium, F-12 medium, a medium which comprises an equivalent volume of Dulbecco's modified minimum essential medium and F-12 medium and the like. Among them, bMEM and DM-160 medium are preferred. The "animal cell lines" include cultured animal cell lines. Examples of the animal cell lines which can grow in a substantially protein-free medium include Vero-317 cell line derived from African green monkey kidney, L-P3 cell line derived from a mouse, HeLa-P3 cell line derived from human cervix carcinoma (the above cell lines are available from The Institute of Physical and Chemical Research Cell Bank), CHL-1 cell line derived from Chinese hamster, CHD-3A cell line (R. G. Ham., Proc. Natl. Acad. Sci. USA., 53:288-293, 1965) and the like. Among them, Vero-317 cell line is preferred.

Then, a substance capable of enhancing replication of exogenous genes is prepared. The "exogenous genes" includes genes to be transfected from the outside of a host cell into the host cell wherein the genes are derived from a different line or from the same line as that of the host cell. The substances capable of enhancing replication of exogenous genes include any substance which is capable of enhancing replication of exogenous genes in transfected cells to replicate at least one copy of the genes. Examples of the substances capable of enhancing replication of exogenous genes include large T antigen derived from SV40 virus, large T antigen derived from polyoma virus, a DNA which contains a gene coding for large T antigen derived from SV40 virus, a DNA which contains a gene coding for large T antigen derived from polyoma virus and Baculo virus DNA. Among them, a DNA which contains a gene coding for large T antigen derived from SV40 virus is preferred. If the substance capable of enhancing replication of exogenous genes is a DNA derived from a virus, it is preferred that the DNA does not contain any origin of DNA replication. Examples of the DNAs which contain a gene coding for large T antigen include SV40 virus DNA (available from Bethesda Research Laboratories Co.) and plasmid pSvtsA58ori(−) (available from The Institute of Physical and Chemical Research DNA Bank). Among them, pSVtsA58ori (−) is preferred.

The DNA which contains a gene coding for large T antigen derived from SV40 virus may be prepared as follows. A DNA fragment which contains a gene coding for large T antigen is prepared by completely digesting SV40 virus DNA with a restriction enzyme which can cleave SV40 virus DNA but not the gene region coding for large T antigen; separating the resulting DNA fragments by agarose gel electrophoresis; and selecting the DNA fragment which contains the gene coding for large T antigen. Examples of the restriction enzymes include Bgl I, Kpn I, EcoRv, AccI, EcoRI, BamHI, TaqI and NdeI. The DNA fragment which contains the gene coding for large T antigen is inserted in a vector DNA to prepare a recombinant DNA. The recombinant DNA can be prepared according to the procedures described in J. Sambrook, E. F. Fritsch and T. Maniatis., Molecular Cloning - A Laboratory Manual, Second edition., Cold Spring Laboratory Press., pp. 1.53-1.73, 1989 (hereinafter referred to as "Molecular Cloning"). Any known vector can be used as a vector DNA. Examples of the vectors include SV40 virus DNA, pSV2- neo (edited by Uchida, Oishi and Furusawa., "Use and Practice Manual of Animal Cells"., PP 388-393, L.I.C. Co., 1984), pSV2-dhfr, pRSVneo, pko-neo, pHyg, pSV2gpt, pMSG, pSVT7, pMT2, BPV-1, pBV-1MTHA, pHEBo, p205, pMT3SV2("Molecular Cloning", Ibid., pp. 16.1–16.81), CDM8 p91023(B), pcDL-SR α296 (Takebe., Experimental Medicine separate volume (edited by Muramatsu and Okamoto., Yodo Co. Tokyo, 1991), pp 292-297), pBR322, pUC12, pUC18, pUC19 ("Molecular Cloning", Ibid., pp. 1.12-1.20 and pp. 4. 10-4.11) and the like. Among the vectors, pBR322 and pUC19 are preferred. DNAs which contain a gene coding for large T antigen derived from a virus other than SV40 can be prepared by repeating the above procedures except that a restriction enzyme which can cleave the selected virus DNA but not the gene region of the large T antigen is used.

Alternatively, SV40 virus DNA per se may be used without inserting it in a vector DNA. Further, DNA fragments which are prepared by completely digesting SV40 virus DNA with a restriction enzyme and DNA fragments which are separated from DNA fragments of SV40 virus DNA completely digested with a restriction enzyme and contain a gene coding for large T antigen, may be used without inserting them in a vector DNA. When SV40 virus DNA or SV40 virus DNA fragment(s) which are completely digested with a restriction enzyme are used, it is preferred that the origin of DNA replication be removed. The same goes for DNAs containing a gene coding for large T antigen derived from a virus other than SV40 virus.

The thus prepared substance capable of enhancing replication of exogenous genes is then introduced into the animal cell which can grow in a substantially protein-free medium. The amount of the substance capable of enhancing replication of exogenous genes introduced into the animal cell is from 0.1 μg to 0.1 mg, preferably from 0.5 to 20 μg per $1 \times 10^5$ cells.

The animal cell is pre-cultured in a medium before the substance capable of enhancing replication of exogenous genes is introduced into it. Examples of the media include a minimum essential medium (hereinafter referred to as "MEM") to which fetal bovine serum, newborn bovine serum, calf serum and/or horse serum and the like are added in a concentration of from 0.5 to 20% (V/V); DM-160 medium; F-12 medium; Dulbecco's modified minimum essential medium and the like. Among the media, MEM to which 5% (V/V) of newborn bovine serum is added is preferred. The animal cell can be cultured in the medium at from 33° to 40° C. for from 1 to 10 days under air containing from 5 to 10% carbon dioxide, preferably at 37° C. for 2 days under air containing 5% carbon dioxide.

The substance capable of enhancing replication of exogenous genes is introduced into the pre-cultured animal cell by a method known to those skilled in the art, which includes electroporation, microinjection, erythrocyte-ghost fusion, liposome fusion, DNA transfection with transfection stimulators and the like. Among the above methods, if the substance capable of enhancing replication of exogenous genes is DNA, DNA transfection with transfection stimulators is preferred. Examples of the transfection stimulators include calcium phosphate, DEAE-dextran, polybrene ("Molecular Cloning", Ibid., pp. 16.30–16.47), lipofectin (available from Bethesda Research Laboratories Co.), DOTMA (available from Boehringer Mannheim Yamanouchi Co., Ltd.) and the like. Among the transfection stimulators, lipofectin is preferred. If the substance capable of enhancing replication of exogenous genes is not DNA, the microinjection method is preferred.

The substance capable of enhancing replication of exogenous genes may be transferred into the animal cell before, after or at the same time as a recombinant DNA obtained by inserting at least one exogenous gene in a vector DNA is transfected into the animal cell. If the substance capable of enhancing replication of exogenous genes is DNA, said DNA may be inserted into a vector DNA into which at least one exogenous gene is inserted and then the resulting recombinant DNA may be transfected into the animal cell. For example, if Baculo virus DNA is used as the substance capable of enhancing replication of exogenous genes, it is possible to insert at least one exogenous gene into a polyhedron gene region of Baculo virus DNA and then to transfect the resulting recombinant DNA into an insect cell.

The animal cell lines which have the substance capable of enhancing replication of exogenous genes can be selected and identified by a method known to those skilled in the art, such as the indirect fluorescent antibody staining technique, drug resistance methods and the like. If drug resistance methods are used, one needs to introduce DNA containing a drug resistance gene into the animal cell at the same time as the substance capable of enhancing replication of exogenous genes is introduced. Examples of the drug resistance genes include neo$^r$ hyg$^r$ gpt, dhfr, CAD, ADA, AS and the like. Among them, neo$^r$ is preferred. The indirect fluorescent antibody staining technique is a preferred method of selection.

The animal cells thus obtained may have the substance capable of enhancing replication of exogenous genes in the cytoplasm. If the substance capable of enhancing replication of exogenous genes is DNA, the substance may or may not be integrated in the nuclear chromosome of the animal cell.

The animal cell thus obtained can grow in a substantially protein-free medium. When exogenous genes are transferred into the animal cell, replication of the exogenous genes is enhanced in the animal cell so that the animal cell produces exogenous gene products in a high yield. The animal cell c n replicate the exogenous genes extrachromosomally.

A transformant can be prepared by transfecting a recombinant DNA containing at least one exogenous gene capable of expression into the animal cell which is capable of growing in a substantially protein-free medium and has the substance capable of enhancing replication of exogenous genes.

The word "expression" means transcribing a DNA sequence corresponding to a gene to a messenger RNA.

Any recombinant DNA which is obtained by inserting at least one exogenous gene capable of expression into a suitable vector can be used in the present invention. The recombinant DNA preferably further contains an entire region or a part of an origin of DNA replication and/or a promotor. Any origin of DNA replication, which starts replication of exogenous genes integrated into the recombinant DNA, can be used as an origin of DNA replication. Among the origins, the origin of DNA replication of SV40 virus is preferred. Examples of the promotors include MMTV-LTR (available from Clonetech Co. as plasmid pMAM neo), TK (available from Japan Mediphysics Co as plasmid pTKGH), mMT-1 (available from Japan Mediphysics Co. as plasmid pXGH5) and the like.

Cycles of replication of exogenous genes in a host cell can be increased by transfecting a recombinant DNA which contains an entire region or a part of an origin of DNA replication and/or a promotor into the host cell.

Examples of the recombinant DNAs include pXGH5, pTKGH, pΦ GH (available from Japan Mediphysics Co.) and the like.

Further, the recombinant DNA can be prepared as follows. At least one exogenous gene capable of expression is first prepared. Examples of the exogenous genes include genes coding for a peptide hormone such as human growth hormone, human insulin, human secretin and human erithropoietin; genes coding for a growth factor such as human platelet-derived growth factor and human epidermal growth factor; genes coding for a protein such as human tissue-plasminogen activator, human albumin and human fibronectin; and oncogenes such as human c-myc gene and human c-ras gene. These genes may be isolated from chromosomal DNAs in a cell such as human hypophysis, pancreas, enteric canal, kidney, bone marrow, blood vessel, liver, spleen or the like. Alternatively, these genes may be enzymatically prepared using, as a template, a messenger RNA which is present in a tumour tissue cell of human esophagus, gaster, spleen, liver, kidney, intestinum crassum, brain, skin or the like. Further, these genes may be chemically synthesized.

At least one exogenous gene capable of expression is inserted as a passenger into a vector DNA such as a plasmid, virus DNA or the like to prepare a recombinant DNA. Examples of the vector DNAs include an entire region or a fragment of DNA derived from SV40 virus; an entire region or a fragment of DNA derived from bovine papilloma virus; an entire region or a fragment of DNA derived from polyoma virus; an entire region or a fragment of DNA derived from L-factor; an entire region or a fragment of DNA derived from adenovirus; an entire region or a fragment of DNA derived from vaccinia virus; an entire region or a fragment of DNA derived from Epstein-Barr virus; an entire region or a fragment of DNA reverse-transcribed from RNA derived from retro-virus and the like. If the animal cell line is derived from a primate cell, the vector DNA is preferably selected from the group consisting of an entire region or a fragment of DNA derived from SV40 virus, an entire region or a fragment of DNA derived from adenovirus, an entire region or a fragment of DNA derived from vaccinia virus, an entire region or a fragment of DNA derived from Epstein-Barr virus, an entire region or a fragment of DNA which is reverse-transcribed from RNA derived from primate retro-virus. If the animal cell line is derived from a bovine cell, the vector DNA is preferably selected from an entire region or a fragment of DNA derived from bovine papilloma virus. If the animal cell line is derived from a rodent cell, the vector DNA is preferably selected from the group consisting of an entire region or a fragment of DNA derived from bovine papilloma virus, an entire region or a fragment of DNA derived from polyoma virus, an entire region or a fragment of DNA derived from L-factor and an entire region or a fragment of DNA which is reverse-transcribed from RNA derived from a rodent retro-virus. The vector DNA preferably contains an origin of DNA replication. Any origin of DNA replication can be used so long as it can start replication of exogenous genes integrated in the recombinant DNA by the substance capable of enhancing replication of exogenous genes. Among them, the origin of DNA replication of SV40 virus is preferred. Specific examples of the vector DNAs include SV40 virus DNA, pSV2- neo, pSV2- dhfr, pko-neo, pSV2 gpt, pMSG, pSVT7, pMT2, BPV-1, pBV-1MTHA, pHEBo, p205, pMT3SV2, CDM8, p91023(B), pcDL-SRα296 and the like. Among the vectors, pSV2-neo is preferred. The above vectors modified when at least one desired exogenous gene is inserted thereinto can also be used so long as they contain a portion which functions as a plasmid and a region which functions as an origin of DNA replication.

At least one exogenous gene can be inserted into the vector DNA as follows. The vector DNA is digested with a restriction enzyme which cleaves the vector DNA at only one site. Then at least one exogenous gene is ligated into the digested vector DNA with a DNA ligase. The procedures are described in detail in "Molecular Cloning", Ibid., pp. 1. 53–1.73. According to the above procedures, a recombinant DNA containing the exogenous gene(s) can be prepared.

A promotor may be further inserted into the recombinant DNA. Examples of the promotors include MMTV-LTR (available from Clonetech Co. as plasmid pMAM neo), TK (available from Japan Mediphysics Co. as plasmid pTKGH), mMT-1 (available from Japan Mediphysics Co. as plasmid pXGH5) and the like. These promotors may be inserted into the recombinant DNA by the same procedures as used in inserting the exogenous gene(s) in the recombinant DNA.

A transformant can be prepared by transfecting the recombinant DNA thus obtained into the animal cell which can grow in a substantially protein-free medium and has a substance capable of enhancing replication of exogenous genes. The amount of the recombinant DNA transfected into the animal cell is from 0.1 to 100 μg, preferably from 1 to 10 μg per $1 \times 10^5$ cells.

The animal cell is pre-cultured in a medium before the recombinant DNA is transfected into it. Examples of the media include MEM to which fetal bovine serum, newborn bovine serum, calf serum and/or horse serum are added in a concentration of from 0.5 to 20% (v/v), DM-160 medium, F-12 medium Dulbecco's modified minimum essential medium and the like. Among the media, MEM to which 5% (v/V) of newborn bovine serum is added is preferred. The animal cell can be cultured in the medium at from 32° to 40° C. for from 1 to 10 days under air containing from 5 to 10% carbon dioxide, preferably at 37° C. for 2 days under air containing 5% carbon dioxide.

The recombinant DNA is transfected into the pre-cultured animal cell by a method known to those skilled in the art, which includes DNA transfection with transfection stimulators, electroporation, microinjection, liposome fusion, erythrocyte-ghost fusion and the like. Among these methods, DNA transfection with transfection stimulators is preferred. Examples of the transfection stimulators include calcium phosphate, DEAE-dextran, polybrene, lipofectin, DOTMA and the like. Among the transfection stimulators, lipofectin is preferred.

Selection and identification of the transformant which is obtained by transfecting the recombinant DNA into the animal cell can be conducted by culturing the transformant in a medium to express the exogenous gene and/or a marker gene of the vector DNA such as auxotrophy and drug resistance.

The transformant thus obtained can grow in a substantially protein-free medium and produce exogenous gene products in a high yield. Further, the transformant can replicate exogenous genes extrachromosomally.

The transformant thus obtained can grow in MEM to which from 0.5 to 20% (V/V) of fetal bovine serum, newborn bovine serum, calf serum, and/or horse serum or the like are added; DM-160 medium; F-12 medium; Dulbecco's modified minimum essential medium, at from 33° to 40° C. for from 1 to 10 days under air containing from 5 to 10% carbon dioxide, preferably in the MEM containing 5% (V/V) of newborn bovine serum at 37° C. for 2 days under air containing 5% carbon dioxide.

Exogenous gene products can be produced by culturing the above transformant in a substantially protein-free medium. The transformant may be cultured from the beginning in a substantially protein-free medium, or may be cultured first in a protein-containing medium and subsequently in a substantially protein-free medium. Preferably, the transformant is cultured first in a protein-containing medium, and then in a substantially protein-free medium. In the latter case, the protein-containing medium is changed to the substantially protein-free medium when the yield of the desired exogenous gene products reaches a maximum. Examples of the protein-containing media include 10% (V/V) fetal bovine serum-containing MEM, 5% (V/V) newborn bovine serum-containing MEM, ASF301 medium and the like. Among the protein-containing media, 5% (v/v) newborn bovine serum-containing MEM is preferred. Examples of the protein-free media include bMEM, DM-160 medium, F-12 medium, a medium which comprises an equivalent volume of Dulbecco's modified minimum essential medium and F-12 medium and the like. Among the protein-free media, bMEM is preferred. A non-essential amino acid such as proline or the like; a vitamin such as ascorbic acid or the like; a hormone such as triiodothyronine or the like may be added to the above medium. These additives can increase the yield of exogenous gene products.

The transformant can be cultured in the medium at from 32° to 40° C. under air containing from 5 to 10% carbon dioxide, preferably at 37° C. under air containing 5% carbon dioxide.

The exogenous gene products can be collected and purified from the culture supernatant as follows. The culture supernatant is dialyzed and concentrated through a dialysis membrane, hollow fiber or the like. Alternatively, ammonium sulfate is added to the culture supernatant to precipitate the exogenous gene products and the resulting precipitate is centrifuged. The crude products thus obtained can be further purified by column chromatography, electrophoresis, gel filtration technique, affinity chromatography or the like. Among these methods, affinity chromatography is preferred.

In one of preferred embodiments of the present invention, a large T antigen gene derived from SV40 virus, which is free of an origin of DNA replication is introduced into Vero-317 cells. The resulting cells are transfected with plasmid pXGH5ori, a recombinant DNA obtained by inserting the origin of DNA replication of SV40 virus into plasmid pXGH5 containing a human growth hormone gene. The transfected cells are then cultured in bMEM to produce human growth hormone.

It is possible to easily produce a great amount of substances useful to mammals by using the transformant of the present invention.

Further, it is easy to collect and purify the substances useful to mammals, which are produced by the transformant of the present invention.

The present invention will be further explained with reference to the following non-limiting examples.

EXAMPLE 1

Figure 2:
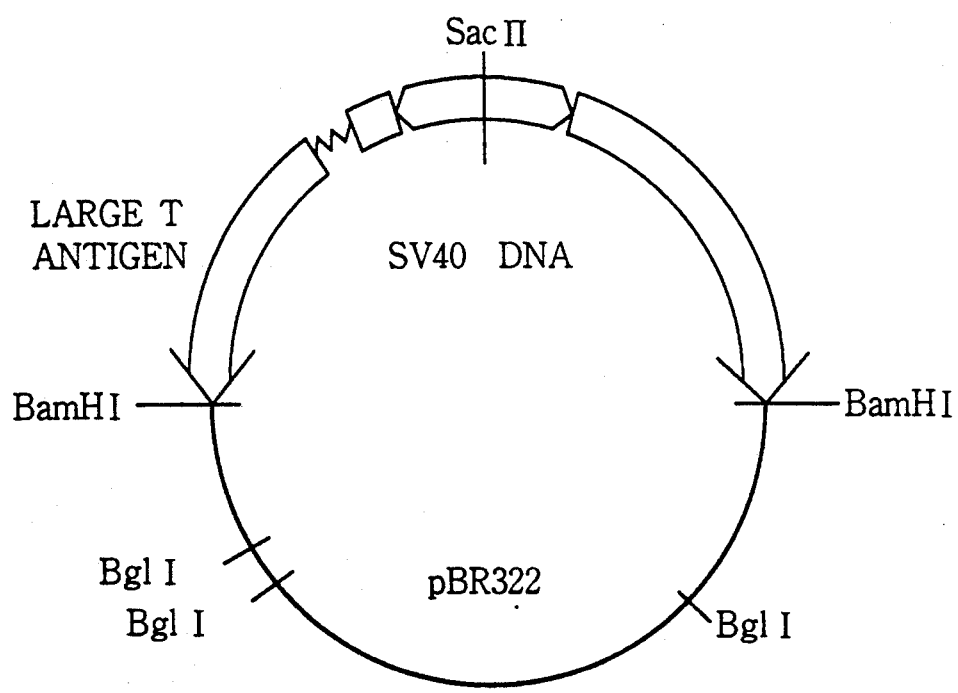
FIG. 2 shows a restriction map of plasmid pSvtsA5-8ori(−)−2.

Introduction of a large T antigen gene derived from SV40 virus into Vero-317 cells $10^6$ cells of Vero-317 cell line (available from The Institute of Physical and Chemical Research Cell Bank) were pre-cultured in 5 ml of MEM to which 5% (V/V) of newborn bovine serum was added (hereinafter referred to as "growth medium") at 37° C. under air containing 5% carbon dioxide for 3 days.

pSVtsA58ori(−) was prepared as follows. Plasmid pSVtsA58 (provided by Associate Professor M. Obinata of The University of Tokyo, Faculty of Pharmaceutical Sciences) which comprises vector pBR322 having inserted thereinto a DNA of temperature-sensitive mutant tsA58 of SV40 virus, was cleaved with restriction enzyme SfiI. The fragments thus obtained (15.6 µg) were digested with Mung Bean Nuclease (available from Takara Shuzo Co., Ltd. 25 units) to create blunt ends. The blunt ends of the fragments were ligated with a DNA ligase. The above procedures were conducted according to the description of "Molecular Cloning", Ibid., pp. 1.53-1.73. The resulting circular DNA was cloned and the cloned DNA which was able to be cleaved at the recombined site with restriction enzyme SacII was selected by procedures described "Molecular Cloning", Ibid., pp. 1.1-1.110. The cloned DNA is plasmid pSVtsA58ori(−). There were two kinds of plasmid pSVtsA58ori(−) in the selected clones. The cloned DNAs were identified as plasmid pSVtsA58ori(−)−1 and plasmid pSVtsA58ori(−)−2. FIG. 1 and FIG. 2 show a restriction map of plasmid pSVtsA58ori(−)−1 and that of plasmid pSvtsA58ori(−)−2, respectively. Plasmid pSVtsA58ori(−)−2 is available to anyone from The Institute of Physical and Chemical Research DNA Bank.

DNA fragments (20 µg) of plasmid pSVtsA58ori(−), which were completely digested with restriction enzymes BamHI and BglI (available from Takara Shuzo Co., Ltd.) and 2 µg of DNA fragments of pSV2-neo (disclosed in C. Gorman, L, Moffat and B. Howard., Mol. Cell. Biol., 2: 1044, 1982 and provided by Professor H. Okada of The University of Osaka, Microbial Disease Institute), which were completely digested with restriction enzymes PvuII and BamHI (available from Takara Shuzo Co.,Ltd.) were dissolved in one ml of mannitol medium. The medium has the composition described in the following Table 1.

TABLE 1

| Composition of Mannitol Medium | |
|---|---|
| Component | content |
| HEPES | 10 mM |
| NaCl | 10 mM |
| Mannitol | 250 mM |
| pH | 7.2 |

The cultured Vero-317 cells were washed with Dulbecco's phosphate buffered saline free from calcium and magnesium (hereinafter referred to as PBS(−)). One ml of 0.25% (W/V) trypsin solution in PBS(−) was added thereto and the trypsin solution was immediately sucked off. The resulting vero-317 cells were maintained at 37° C. for 2-3 minutes. About 200,000 cells of the trypsin-treated Vero-317 cells were suspended in the mannitol medium comprising the DNA fragments of pSVtsA58ori(−) and those of pSV2-neo. The resulting mannitol medium suspension was subjected to 480 V of direct voltage for 1ms on a Pro-Genetor (available from Hoefer Scientific Instruments Co, California, U. S.A.). The application of direct voltage was repeated 5 times at intervals of about 1 minute. Then the suspension was transferred into a 15 ml volume centrifuge tube to centrifuge at 1000 rpm for 3 minutes. After removing the supernatant, 5 ml of the growth medium was added to the remaining precipitate. The resulting suspension was transferred to a culture dish with a 6 cm diameter and a 1 cm height. The Vero-317 cells were cultured under air containing 5% carbon dioxide for 5 days. Then the culture supernatant was removed. The Vero-317 cells were cultured in the growth medium containing antibiotic substance G418 available from Sigma Co.) in a final concentration of 400 µg/ml at 37° C. for 25 days under air containing 5% carbon dioxide. As a result, 23 clonies were grown. A cloning cup was set on each colony and 0.5 ml of 0.25% (W/V) trypsin solution was added thereto. The trypsin solution was immediatly removed and the colonies were incubated at 37° C. for 3-5 minutes. Subsequently, 0.5 ml of the growth medium was added to suspend the cloned cells. Of each of the separately-cloned cells, 1,000 cells were cultured in 0.5 ml of the growth medium at 37° C. for 5 days under air containing 5% carbon dioxide. The resulting cells were fixed with 10% (V/V) formalin -PBS (−) solution for 10 minutes and then washed with 95% (V/V) ethanol solution. Fifty µl of anti-large T antigen monoclonal antibody (provided by Professor N. Yamaguchi, Institute of Medical Science, The University of Tokyo) solution in PBS (−) was added to the cloned cells and the culture solution was maintained at 37° C. for 30 minutes. After the solution was washed out with PBS(−), 50 µl of FITC-labeled anti-mouse Ig G antibody (available from ZYMED Laboratories, Inc.) solution in PBS(−) was added thereto and the culture solution was maintained at 37° C. for 30 minutes. The culture was washed out with PBS(−) and then the clones which expressed large T antigen were detected under a fluorescence microscope (available from Olympus Co.). Three clones were obtained, which were named verots S1, Verots S2 and Verots S3, respectively.

Verots S3 has been deposited as FERM BP-3370 under the terms of the Budapest Treaty with Fermentation Research Institute (1-3, Higashi 1 chome Tsukubashi Ibaraki-ken 305, JAPAN) on Sep. 25, 1990. Verots-S-1 and Verots-S2 were deposited on Jan. 7, 1991, under the accession numbers FERM BP-4144 and FERM BP-4162, respectively, under the Budapest Treaty. All restrictions on the availability to the public of the deposited cells will be irrevocably removed upon the granting of the patent to the present application.

Each $3 \times 10^4$ cells of parent Vero-317 cells or Verots S3 cells were seeded in a culture dish with a 3.5 cm diameter and a 0.5 cm height. After the cells attached on the culture surface, the cells were washed with bMEM and 5 ml of bMEM was finally added thereto. The cells were cultured at 37° C. for 7 days under air containing 5% carbon dioxide. During the culture, the growth rate of the cells was determined as follows.

After the cultured cells were washed with PBS(−), 0.25% (V/V) trypsin solution was added thereto in an amount of 0.1 ml per 1 cm² culture surface and the culture solution was maintained at 37° C. for 5 minutes. After the cells were dispersed, the number of cells was counted by using a Hemocytometer (TATAI). The results are shown in Table 2.

TABLE 2

| Cell Line | Growth Rate of Cells<br>The Number of Cells after 7 Days |
|---|---|
| Vero-317 | $1.7 \times 10^5$ |
| Verots S3 | $2.0 \times 10^5$ |

After culturing the above three clones and parent vero-317 cells in bMEM at 37° C. for 7 days under air containing 5% carbon dioxide, expression of large T antigen was detected by the above method. The results are shown in Table 3.

TABLE 3

| Cell Line | Expression of Large T Antigen |
|---|---|
| Vero-317 | − |
| Verots S1 | ++ |
| Verots S2 | ++ |
| Verost S3 | ++ |

−: Expression of Large T antigen was not observed.
++: Expression of Large T antigen was observed.

The results shown in Table 2 and Table 3 reveal that Verots S3 cells were grown in bMEM with comparable proliferation potency as that of Vero-317 cells. Almost the same level of expression of large T antigen in Verots S1, Verots S2 or Verots S3 was observed when the medium was changed from the growth medium to bMEM.

EXAMPLE 2

Production Of human growth hormone by the transformant of Verots S1 cell, Verots S2 cell or Verots S3 cell Plasmid pXGH5ori which was obtained by inserting the origin of DNA replication of SV40 virus into plasmid pXGH5 (available from Japan Mediphysics Co.) containing a human growth hormone gene was prepared as follows.

After digesting pSV2- neo with HindIII and PvuII (available from Takara Shuzo Co., Ltd.), 330 bp DNA fragment was obtained by agarose gel electrophoresis. The DNA fragment of pSV2- neo was ligated at the PvuII site to a DNA fragment of

5'-C T C G A G-3'

3'-G A G C T C-5' which was synthesized by a DNA synthesizer (available from Applied Biosystems Co.) with a DNA ligase and then the resulting DNA was digested with restriction enzyme XhoI (available from Takara Shuzo Co., Ltd.).

Figure 3:
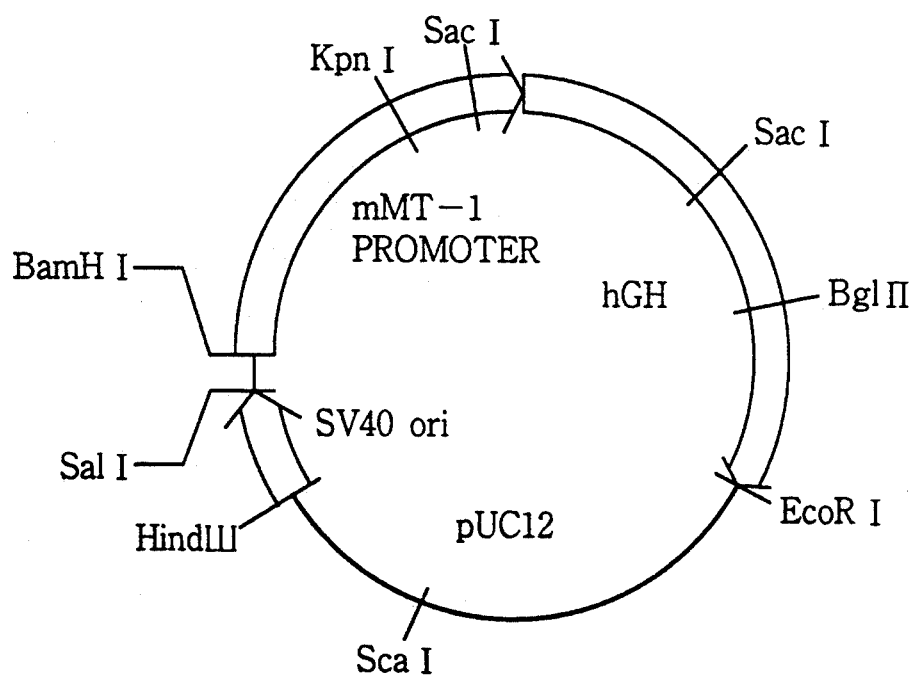
FIG. 3 shows a restriction map of plasmid pXGH5ori.

On the other hand, pXGH5 was digested with restriction enzymes HindIII and SalI (available from Takara Shuzo Co., Ltd.) and then 6.7 kb DNA fragment was obtained by agarose gel electrophoresis. The 6.7 kb DNA fragment was mixed with the DNA fragments which were obtained by digesting the DNA with XhoI. The mixed DNA fragments were ligated together with a DNA ligase to obtain pXGH5ori. The ligation with the DNA ligase was conducted according to the description of "Molecular Cloning", Ibid., pp. 1.53–1.73. FIG. 3 shows a restriction map of plasmid pXGH5ori.

Twenty μg of plasmid pXGH5ori was dissolved in 1.5 ml of bMEM. Fifty μg of DNA transfection stimulator lipofectin (available from Bethesda Research Laboratories Co.) was dissolved in 1.5 ml of bMEM. After the medium was removed from the culture dish with a 6 cm diameter and a 1 cm height containing about 1,000,000 cells of Verots S1 and 3 ml of bMEM, the bMEM containing plasmid pXGH5ori and the bMEM containing lipofectin were together added to the culuture dish. The cells were cultured for 6 hours at 33° C. under air containing 5% carbon dioxide and then the culture supernatant was removed. Four ml of growth medium was added to the remainder and the cells were cultured for more than 24 hours at 33° C. under air containing 5% carbon dioxide. The growth medium was changed every 24 hours. The culture surpernatant (100 μl) was sampled to measure the concentration of human growth hormone by using the Tran-GES kit (available from Japan Mediphysics Co.).

The above procedures were repeated with Vero-317 cells, Verots S2 cells and Verots S3 cells. Further, the above procedures were repeated with COS-1 cells (available from The Institute of Physical and Chemical Research Cell Bank) as a control for comparison. The results are shown in Table 4.

TABLE 4

| Cell Line | Yield of Human Growth Hormone | |
|---|---|---|
| | Days after Transfection (day) | Concentration of Human Growth Hormone (ng/ml) |
| COS-1 | 2 | 35.7 |
| | 4 | 175.9 |
| | 7 | 124.6 |
| Vero-317 | 2 | 6.8 |
| | 4 | 24.7 |
| | 7 | 29.2 |
| Verots S1 | 2 | 14.6 |
| | 4 | 173.1 |
| | 7 | 290.0 |
| Verots S2 | 2 | 11.4 |
| | 4 | 60.4 |
| | 7 | 131.3 |
| Verots S3 | 2 | 36.4 |
| | 4 | 466.1 |
| | 7 | 631.9 |

The results shown in Table 4 reveal that Verots S3 cells produced a greater amount of human growth hormone more than 4 days after transfection of the plasmid than COS-1 cells did. COS-1 cells have been widely known to constitutively express large T antigen.

EXAMPLE 3

Production of human growth hormone by the transformant of Verots S3 cell

Plasmid pXGH5ori was transfected into Verots S3 cells and the resulting transformants were cultured at 33° C. or 37° C. in the same procedures as in Example 2.

COS-7 cells (available from The Institute of Physical and Chemical Research Cell Bank) were used as a control for comparison.

Yields of human growth hormone produced by the above transformants are shown in Table 5.

TABLE 5

| Days after Transfection (Day) | Verots S3 cells 33° C. | Verots S3 cells 37° C. | COS-7 cells 33° C. | COS-7 cells 37° C. |
|---|---|---|---|---|
| 0 | 0.000 | 0.000 | 0.000 | 0.000 |
| 1 | 41.753 | 163.402 | 4.833 | 13.845 |
| 2 | 284.021 | 611.512 | 44.540 | 273.380 |
| 3 | 619.158 | 793.213 | 163.793 | 494.253 |
| 4 | 923.196 | 790.206 | 240.988 | 575.235 |
| 5 | 864.949 | 561.684 | 280.956 | |
| 6 | 994.478 | 458.247 | 288.271 | 387.539 |
| 8 | 1016.495 | 267.698 | 288.924 | 231.583 |
| 10 | 871.650 | 181.959 | 221.787 | 121.347 | unit: ng/ml

EXAMPLE 4

Production of human growth hormone by the transformant of Verots S3 cell (Comparison of plasmids pXGH5 and pXGH5ori)

Plasmid pXGH5 or pXGH5ori was transfected into Verots S3 cells and the resulting transformants were cultured in the same procedures as in Example 2.

Yields of human growth hormone produced by the above transformants are shown in Table 6.

TABLE 6

| Transfected Plasmid | Days after Transfection (day) | Concentration of Human Growth Hormone in the Medium (ng/ml) |
|---|---|---|
| pXGH5 | 2 | 2.0 ng/ml |
| | 4 | 5.5 |
| pXGH5ori | 2 | 110.7 |
| | 4 | 301.5 |

The results shown in Table 6 reveal that the transformant which was transfected with the plasmid containing the origin of DNA replication produced human growth hormone in a higher yield.

EXAMPLE 5

Production of human growth hormone by the transformant of Verots S3 cell (The medium was changed from growth medium to bMEM)

The procedures of Example 4 were repeated except that the serum-containing growth medium was replaced by bMEM 5 days after the transfection of the plasmid and then the bMEM was exchanged with a fresh bMEM every 24 hours.

Yields of human growth hormone produced by the transformants of Verots S3 cells under the above culture conditions are shown in Table 7.

TABLE 7

| Transfected Plasmid | Days after Transfection (day) | Concentration of Human Growth Hormone in the Medium (ng/ml) |
|---|---|---|
| pXGH5 | 5 | 9.6 |
| | 6 | 9.2 |
| | 8 | — |
| | 11 | 4.1 |
| pXGH5ori | 5 | 361.8 |
| | 6 | 401.0 |
| | 8 | 43.9 |
| | 11 | 44.8 |

The data after 5 days show concentrations of human growth hormone produced by the above transformants in the serum-containing growth medium. A concentration of human growth hormone produced by pXGH5-transfected Verots S3 cells 8 days after the transfection was not measured.

The results shown in Table 7 show that all the transformants produced human growth hormone in a high yield 6 days after the transfection. Even 11 days after the transfection, pXGH5ori-transfected Verots S3 cells had a yield of human growth hormone 10 times higher than that of pXGH5-transfected Verots S3 cells.

The present invention has been illustrated by means of illustrative working examples and preferred embodiments, but one of ordinary skill in the art will recognize that modifications and improvements may be made while remaining within the scope on spirit of the present invention. The scope of the invention is determined solely by the appended claims.

We claim:

1. An animal cell line useful for the expression of exogenous gene in a substantially protein-free medium, comprising: a DNA replication origin of SV40 in a cell that is derived from precultured Vero-317 and which expresses T antigen as a SV40 gene product.

2. An animal cell line according to claim 1, wherein the cell is selected from the group consisting of Verots-S1, Verots-S2, and Verots-S3.

3. An animal cell line according to claim 1, wherein the cell is Verots-S3.

4. A transformant obtained by transfecting an animal cell according to claim 1 by a recombinant DNA comprising: DNA replication origin of SV40 and at least one gene encoding a protein or peptide wherein said transformant is able to express protein or peptide in a substantially protein-free medium.

5. A transformant according to claim 4 obtained by transfected Verots-S3.

6. A transformant according to claim 4, wherein the recombinant DNA is pXGH5ori.

7. A method for producing a transfected gene product which comprises the steps of:
   (a) activating Vero-317 cells that express T antigen as a SV40 gene product in a protein-containing medium;
   (b) transfecting the cells with a recombinant DNA comprising DNA replication origin of SV40 and at least one gene encoding a protein or peptide;
   (c) cultivating the transformant obtained in the step (b) in a substantially protein-free medium; and
   (d) recovering the gene product from the cultured medium.

* * * * *

UNITED STATES PATENT AND TRADEMARK OFFICE
CERTIFICATE OF CORRECTION

PATENT NO. : 5,254,462
DATED : October 19, 1993
INVENTOR(S) : Tadao Ohno et al.

It is certified that error appears in the above-indentified patent and that said Letters Patent is hereby corrected as shown below:

On the title page, Item [19] and [75],

The first inventor's name should read:

Item [19], -- Ohno et al.--

Item [75], --Tadao Ohno--

Signed and Sealed this

Twelfth Day of April, 1994

Attest:

BRUCE LEHMAN

Attesting Officer     Commissioner of Patents and Trademarks